United States Patent
Lohrmann et al.

(10) Patent No.: US 6,193,953 B1
(45) Date of Patent: *Feb. 27, 2001

(54) STABILIZED MICROPARTICLES AND THEIR USE AS ULTRASOUND CONTRAST AGENTS

(75) Inventors: Rolf Lohrmann, La Jolla; Brent Lee Golec, San Diego, both of CA (US)

(73) Assignee: Molecular Biosystems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/521,529

(22) Filed: Mar. 8, 2000

Related U.S. Application Data

(63) Continuation of application No. 08/951,710, filed on Oct. 16, 1997, now Pat. No. 6,083,484, which is a continuation-in-part of application No. 08/735,594, filed on Oct. 17, 1996, now abandoned.

(51) Int. Cl.[7] .................................................. A61B 8/13
(52) U.S. Cl. ........................... 424/9.52; 424/491; 424/499
(58) Field of Search .................................. 424/9.51, 9.52, 424/491, 499; 600/431

(56) References Cited

U.S. PATENT DOCUMENTS

| | | | |
|---|---|---|---|
| 4,718,433 | 1/1988 | Feinstein | 424/9.52 |
| 4,774,958 | 10/1988 | Feinstein | 424/9.52 |
| 4,957,656 | 9/1990 | Cerny et al. | 424/9.52 |
| 5,149,543 | 9/1992 | Cohen et al. | 424/499 |
| 5,216,130 | 6/1993 | Line et al. | 530/362 |
| 5,225,282 | 7/1993 | Chagnon et al. | 428/407 |
| 5,308,701 | 5/1994 | Cohen et al. | 428/402.22 |
| 5,364,612 | 11/1994 | Goldenberg | 424/1.53 |
| 5,409,688 | 4/1995 | Quay | 424/9 |
| 5,413,774 | 5/1995 | Schneider et al. | 424/9.51 |
| 5,505,932 | 4/1996 | Grinstaff et al. | 424/9.3 |
| 5,562,099 | 10/1996 | Cohen et al. | 128/662.02 |

FOREIGN PATENT DOCUMENTS

| | | |
|---|---|---|
| WO 92/05806 | 4/1992 | (WO) . |
| WO 92/17213 | 10/1992 | (WO) . |
| WO 92/19749 | 11/1992 | (WO) . |
| WO 94/06477 | 3/1994 | (WO) . |
| WO 94/18954 | 9/1994 | (WO) . |
| WO95/01187 | 1/1995 | (WO) . |
| WO 95/23615 | 9/1995 | (WO) . |

OTHER PUBLICATIONS

Ashwell and Morell (1974). "The role of Surface Carbohydrates in the Hepatic Recognition and Transport of Circulating Glycoproteins," *Adv Enzymol* (Meister, ed, Interscience Publication) 41:99–128.

(List continued on next page.)

*Primary Examiner*—Gary E. Hollinden
(74) *Attorney, Agent, or Firm*—Morrison & Forrester, LLP

(57) ABSTRACT

Microparticles useful for enhancing the ultrasound image of a tissue or organ consist of liquid and/or gas core material which is encapsulated by a biocompatible, tanned protein shell. These stabilized microparticles are useful as ultrasonic imaging agents, and are additionally useful in the further production of functionalized microparticles for in vivo imaging. In particular, targeting molecules such as antibodies or other ligands can be attached to the strengthened exterior surface of the stabilized microparticles to impart target-specificity to the microparticles. The targeting molecules may also provide hydrophilicity to the exterior surface, thus increasing the recirculation time of the microparticles. The targeting molecules may be attached directly to the exterior surface of the microparticles, or they may be attached via a bifunctional spacer arm, which may itself be hydrophilic. The target-specific microparticles are injected intravenously, allowed to accumulate at the target site, and used to enhance the ultrasound image of a target tissue or organ.

13 Claims, 3 Drawing Sheets

OTHER PUBLICATIONS

Ashwell and Harford (1982). "Carbohydrate–Specific Receptors of the Liver," *Ann Rev Biochem* 51:531–554.

Beuth, et al. (1987). "Inhibition of Liver Metastasis in Mice by Blocking Hepatocyte Lectins with Arabinogalactan Infusions and D–Galactose," *Cancer Res Clin Oncol* 13:51–55.

Bini, et al. (1989). "Identification and Distribution of Fibrinogen, Fibrin, and Fibrin(ogen) Degradation Products in Atherosclerosis," 9(1):109–121.

deJong, et al. (1993). "Quantification of Transpulmonary Echocontacts effects," *Ultrasound in Med Biol* 19(4):279–288.

Grinstaff, M.W. et al. (1991). "Air–Filled Proteinaceous Microbubbles: Synthesis of an Echo–Contrast Agent," *Proc. Natl Acad Sci USA* 88(17):7708–7710.

Grinstaff, M.W. et al. (1992). "Proteinaceous Microsperes," ACS Symposium Series 493:218–226.

Goldenberg, et al. (1992). "Radioimmunodetection in Cancer Identification," *J Nucl Med* 33(5):803–814.

Heidemann (1990). *"Leather" Ullmann's Encyclopedia of Industrial Chemistry,* 5th ed, Elvers et al. eds., A15:259–274 (VCH Publishers, New York).

Josephson, et al. (1990). "A Functionalized Superparamagnetic Iron Oxide Colloid as a Receptor Directed MR Contrast Agent," *Mag Res Imag* 8:637–646.

Knight (1998). "Imaging Thrombi with Radiolabeled Anti–Fibrin MonoclonalAntibodies," *Nucl Med Comm* 9:823–829.

Laakso, et al. (1986). "Acrulic Microspheres In Vivo. X. Elimination of Circulating Cells By Active Targeting Using Specific Monoclonal Antibodies Bound to Microparticles," *Life Science* 38(2):183–190.

Lasic, et al. (1991). "Sterically Stabilized Liposomes: A Hypothesis on the Molecular Origin of the Extended Circulation Times," *Biochim Biophys Acta* 1070:187–192.

Longo, et al. (1982). "Preparation of Hydrophilic Albumin Microspheres Using Polymeric Dispersing Agents," *J Pharm Sci* 71(12):1323–1328.

Milenic, et al. (1991). "Construction, Binding Properties, Metabolism and Tumor Targeting of a Single Chain Fv Derived from the Pancarinoma Monoclonal Antibody CC49," *Cancer Res* 51:6363–6371.

Ojima, et al. (1995). "Antithrombotic Agents: From RGD to Peptide Mimetics," *BioorganicMed Chem* 3(4):337–360.

Ophir, et al. (1989). "Contrasts Agents in Diagnostic Ultrasound," *Ultrasound in Med and Biol* 19)4):319–333.

Wang, et al. (1991). "A Monoclonal Antybody Reacting with Platelets for Monitoring Thrombolysis," *Nucl Med Biol* 18(3):275–280.

Wigglesworth, (1990). *J Insect Physiol* 36(5):307–314. Abstract only.

General Formulas of Activated PEGs $$YO(CH_2CH_2O)_nCH_2CH_2Z \quad n=20-450$$

| Y= | Z= |
|---|---|
| 1) CO–NHS | 1) OCH$_3$ |
| 2) (CH$_2$)$_m$CO–NHS  m=1–3 | 2) OH |
| 3) CO(CH$_2$)$_m$CO–NHS  m=2,3 | 3) SS– |
| 4)  | 4) NHCOCH$_2$CH$_2$SS– |
| 5) CH$_2$CH—CH$_2$ (epoxide) | 5) NHCOCH$_2$CH$_2$– |
| 6)  SCH$_2$CF$_3$ | 6)  S–CH=CH$_2$ |

NHS = O–N(succinimide)

STABILIZED MICROPARTICLES AND THEIR USE AS ULTRASOUND CONTRAST AGENTS

Therefore, this application is a continuation of U.S. Ser. No. 08/951,710, filed Oct. 16, 1997, U.S. Pat. No. 6,083,484 which is a continuation-in-part of U.S. Ser. No. 08/735,594, filed Oct. 17, 1996, the specifications of which are incorporated herein in their entirety.

TECHNICAL FIELD

This invention is in the field of ultrasound contrast agents. More particularly, it concerns the production of stabilized microparticles which can be used as ultrasound contrast agents. The ultrasound contrast agents can be further characterized as consisting of suspensions of microparticles of a gas and/or liquid encapsulated by a shell of a proteinaceous material whose exterior surface has been "tanned" subsequent to microparticle formation.

BACKGROUND ART

Diagnostic ultrasonic imaging is based on the principle that waves of sound energy can be focused upon an area of interest and reflected in such a way as to produce an image thereof. The ultrasonic transducer is placed on a body surface overlying the area to be imaged, and ultrasonic energy in the form of sound waves is directed toward that area As ultrasonic energy travels through the body, the velocity of the energy and acoustic properties of the body tissue and substances encountered by the energy determine the degree of absorption, scattering, transmission and reflection of the ultrasonic energy. The transducer then detects the amount and characteristics of the reflected ultrasonic energy and translates the data into images.

As ultrasound waves move through one substance to another there is some degree of reflection at the interface. The degree of reflection is related to the acoustic properties of the substances defining the interface. If these acoustic properties differ, such as with liquid-solid or liquid-gas interfaces, the degree of reflection is enhanced. For this reason, gas-containing contrast agents are particularly efficient at reflecting ultrasound waves. Thus, such contrast agents intensify the degree of reflectivity of substances encountered and enhance the definition of ultrasonic images.

Ophir and Parker describe two types of gas-containing imaging agents: (1) free gas bubbles; and (2) encapsulated gas bubbles (*Ultrasound in Medicine and Biology* 15(4):319–333 (1989)), the latter having been developed in an attempt to overcome instability and toxicity problems encountered using the former. Encapsulated gas bubbles, hereinafter referred to as "microspheres," are composed of a microbubble of gas surrounded by a shell of protein or other biocompatible material. One such imaging agent is ALBUNEX® (Molecular Biosystems, Inc., San Diego, Calif.) which consists of a suspension of air-filled albumin microspheres. Microspheres are part of the broader category of imaging agents referred to herein as "microparticles," which intends hollow vessels of gas and/or liquid encapsulated by a shell.

Generally, microparticles of a particular gas in the form of protein-shelled microspheres exhibit improved in vivo stability when compared to free bubbles of the same gas. However, most protein-shelled microspheres still have relatively short in vivo half lives which compromise their usefulness as contrast agents. This instability in vivo was thought to result from the collapse or breakdown of the protein shells under pressure resulting in rapid diffusion of the gas from the microspheres. Thus, many recent efforts have centered on improvements to the protein shell as a way of increasing in vivo pressure stability, such as coating the protein shell with surfactants (Giddy, WO 92/05806), binding the protein with a protein-reactive aldehyde (Feinstein et al., U.S. Pat. No. 4,718,433 and U.S. Pat. No. 4,774,958), covalently cross-linking the protein shell (Holmes et al., WO 92/17213) and ionically cross-linking the protein shell (Klaveness et al., WO 95/23615).

Efforts to stabilize microspheres also include the use of gases other than air, since air-filled microspheres have been shown to quickly lose echogenicity when subjected to pressure changes of 150 mm Hg, such as would be encountered during injection and circulation in vivo (N. deJong, et al., *Ultrasound Med. Biol.* 19:279–288, 1993.) U.S. Pat. No. 5,413,774 indicates that the pressure resistance of microspheres can be improved by using at least a portion of gas that has a $S_{gas}/\sqrt{MW_{gas}} \leq 0.0031$, where $S_{gas}$ is the water solubility of the gas and $MW_{gas}$ is the average molecular weight of the gas.

PCT Application WO 95/01187, published Jan. 12, 1995, describes pressure-stable microspheres of gas encapsulated by a heat-insolubilized filmogenic protein wherein the encapsulated gas is entirely a water insoluble gas. Among the gases specifically mentioned are the perfluoroalkanes $CF_4$, $C_2F_6$, $C_3F_8$, and $C_4F_{10}$. These microspheres are made by subjecting a mixture of an aqueous solution of the protein and the insoluble gas to ultrasonic or mechanical cavitation in the absence of oxygen by sonicating or milling the mixture in a sonicator/mill that is closed to the atmosphere.

Although the encapsulated gas may be an important factor in determining microparticle stability, the composition and flexibility of the microparticle shell is equally important. In addition to its influence on in vivo stability, the shell composition greatly influences the ability of a microparticle to withstand further processing after formation, i.e. "post-processing." This can include routine manufacturing procedures, such as sterilization and packaging, as well as additional chemical manipulations. For example, it may be desirable to perform the chemical steps necessary to attach targeting moieties such as antibodies to the microparticle shell after formation.

It is well known in the art to target therapeutic or diagnostic agents to specific tissue or organs to enhance the efficacy of such agents. Antibodies have been used extensively to target cytotoxic agents or detectable labels to cancers. For instance, radioimmunodetection techniques employing radiolabeled antibodies to various cancer types have been employed to detect and image cancerous tissue. Similarly, toxins such as ricin have been conjugated to antibodies specific to cancer to produce cancer-specific immunotoxins. Antibodies have also been bound to particulate materials such as liposomes and albumin particles. In this regard, U.S. Pat. No. 5,216,130 describes Tc-99m-labeled albumin microspheres conjugated to IgG via dextran spacer arms.

In addition to antibodies, other ligands that are specific to receptors on particular cell types have been used to target agents to such cells. For instance, it is known that hepatocytes possess plasma membrane receptors for glycoproteins whose oligosaccharide chains have β-linked galactose or N-acetylgalactosamine terminals (Ashwell, G. et al. *Adv. Enzymol.* 41:99 (1974) and *Ann. Rev. Biochem.* 51:531 (1982)). Liposomes and magnetic particles whose surfaces have been galactosylated or coated with arabinogalactan are rendered hepatocyte-specific. Such magnetic particles have been shown to be useful as MRI agents for imaging the liver (Josephson, L. et al., *Mag. Res. Imag.* 8:637–646 (1990)). Asialoglycoproteins have also been conjugated to genes to target genes to hepatocytes (PCT/US 92/03639).

Although attaching functional moieties such as antibodies to gas and/or liquid-filled microparticles for use as imaging agents has been previously described (see, for example, PCT Application WO 95/01187), no such protein-shelled microparticles have yet been successfully manufactured for use as in vivo imaging agents. This is partly due to the fragility of the microparticle shells which are incapable of withstanding the physical and chemical conditions which are necessary to make such attachments. Furthermore, such efforts have resulted in shells lacking the ability to recirculate.

It is therefore an object of the present invention to provide non-toxic microparticles with tanned protein shells. These stabilized protein-shelled microparticles are useful as in vivo imaging agents having flexible shells capable of traveling through the capillary system, and which can also serve as intermediates for the production of functionalized microparticles. It is a further object of the present invention to provide processes for the formation of these stabilized microparticles, and processes for the formation of microparticles having functional moieties attached thereto utilizing these stabilized microparticles.

DISCLOSURE OF THE INVENTION

The present invention provides stabilized microspheres whose shells have been tanned using metal salt solutions. In particular, the present invention provides for a process of producing biocompatible microspheres comprising gas and/or liquid cores and stabilized shells. The shells are characterized as being sturdy, yet flexible, thus enabling for greatly enhanced in vivo and in vitro stability, increased ability to withstand chemical and physical post-processing, and capacity to endure heat sterilization.

The process is carried out on proteinaceous microparticle preparations with tanning methods using metal salt solutions. The preferred metals are chromium, zirconium, titanium and aluminum. The process parameters may be varied in order to achieve the desired amount of tanning over any given period of time. The degree of tanning is dependent upon the concentration of the metal salt, duration and temperature of the reaction. The preferred concentrations of metal salt solutions generally range from 1–30 mM with temperatures of up to approximately 160° C. for a few minutes to several hours or more.

The tanned microspheres may further be processed in order to hydrophilize the shell and/or attach targeting moieties. The hydrophilic functional moieties may include polysaccharides, PEGs, and peptides, for example.

A targeting moiety may be attached to the tanned microparticle shell. The targeting moiety may have a special affinity for intravascular or extravascular targets including the hepatocytes of the liver, certain cancers, and other tissues and/or organs. These targeted agents may be administered in any suitable manner, including intravenously, rectally or intravaginally. Some targeting moieties may serve a dual purpose as a diagnostic targeting tool as well as a therapeutic delivery vehicle. Bifunctional spacer arms may also be employed to attach to the exterior surface of the shell and to the targeting moiety.

The resulting microparticle preparations are non-toxic and are capable of traveling through the capillary system. The enhanced stability results in their ability to accumulate at a particular site for improved imaging and potential therapeutic delivery. Furthermore, the longevity of the microparticles aids in the ability to perform organ perfusion studies.

BEST MODE FOR CARRYING OUT THE INVENTION

Figure 1:
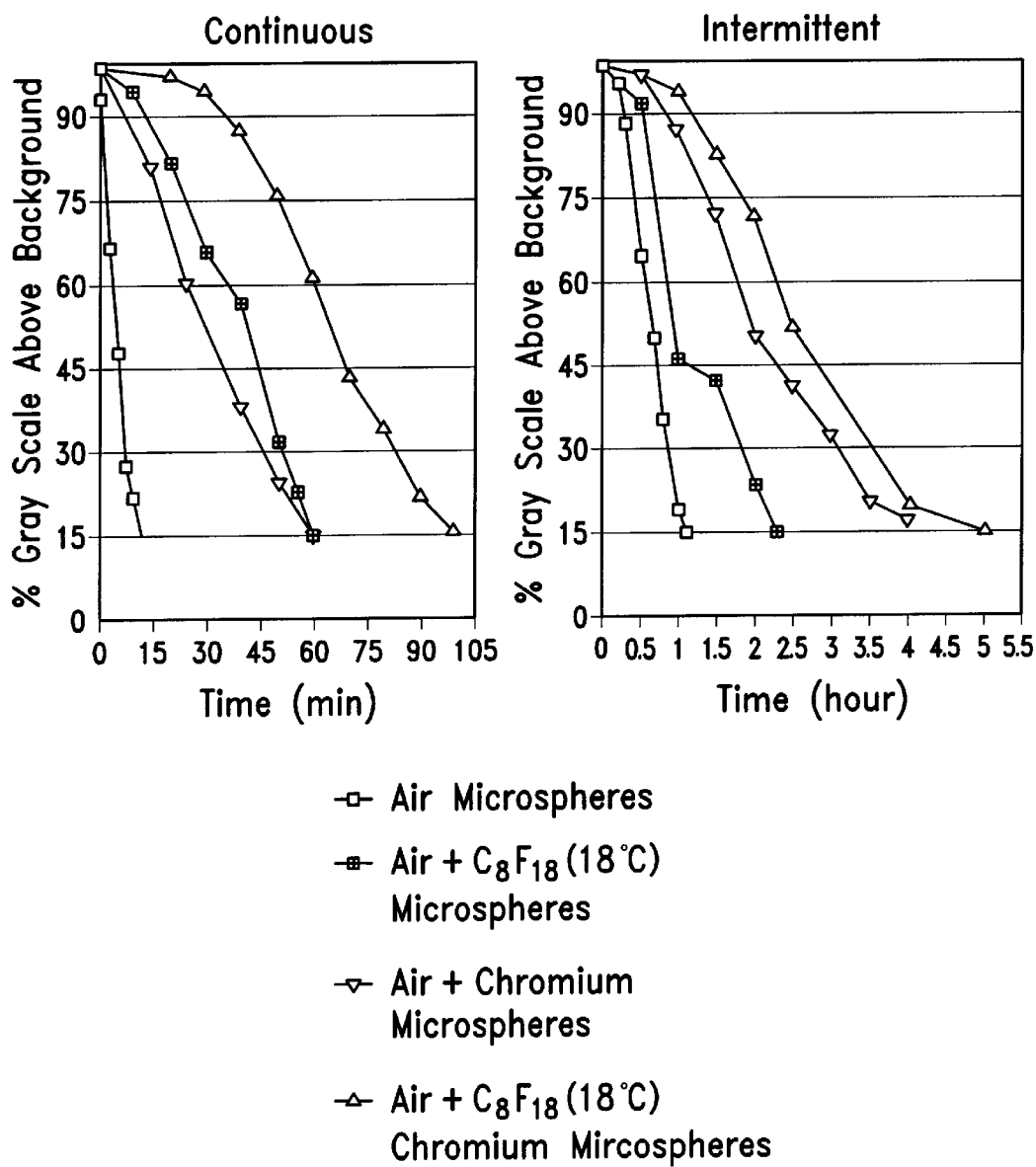
FIG. 1 depicts the in vitro stability of various microsphere preparations.

The stabilized microparticles of the present invention are characterized as having proteinaceous shells whose exterior surfaces have been tanned. This refers to the use of metal salts to form polynuclear coordination complexes between the ionized carboxyl groups of the surface-exposed amino acids and bridging ligands. Although tanning methods have enjoyed wide use in the leather industry, their utility for the production of in vivo agents has only now been discovered. When the method is used on existing microparticle preparations, the result is a biocompatible ultrasound imaging agent having increased in vivo longevity, and being capable of withstanding rigorous heat and chemical post-processing reactions while maintaining shell elasticity.

The tanned microparticles are non-toxic. For example, it is estimated that a typical tanned microparticle preparation contains approximately 45 $\mu$g of bound trivalent chromium per mL of microsphere suspension based on inductively coupled plasma emission spectroscopy (ICP) of isolated microspheres. The metal content is variable, depending on the tanning process parameters. As the microspheres are metabolized, the bound chromium is released into the bloodstream. Blood has a high binding capacity for chromium, where it is bound to serum protein. As chromium is an essential mineral, the U.S. Food and Nutrition Board has recommended a safe and adequate dietary intake of 50–200 $\mu$g of chromium per day. It is normally excreted rapidly through the kidneys, with some excretion through the biliary system.

These stabilized microparticles are useful as ultrasound imaging agents, and in the further production of functionalized microparticles. "Functionalized microparticles" are characterized by having functional moieties attached to their exterior surfaces. "Functional moieties" intends chemical moieties or substituents which serve to alter or enhance the biological interactions of the microparticles, in vivo.

The stabilized microparticles may be functionalized to increase their recirculation time in vivo by attaching hydrophilic functional groups. Such microparticles are referred to herein as "hydrophilic microparticles." Alternatively, the tanned microparticles may be functionalized to render them specific for a particular tissue or organ, in which case the functional moieties are targeting moieties. Such microparticles are referred to herein as "target-specific microparticles." Preferably, the stabilized microparticles are functionalized by attaching the same or different functional moieties to render them both hydrophilic and target-specific.

The microparticles of the present invention comprise a core material encapsulated by a shell. Depending on the nature of the material in the core (i.e. gas and/or liquid) and the rigidity of the shell, they may be largely spherical, or they may have an irregular aspherical shape.

For use as ultrasound contrast agents in vivo, the microparticles must also be non-toxic, echo reflective, and of a size and flexibility suitable for passage through small blood vessels. Generally, the microparticles will have a mean diameter of between $0.1\mu$ and $10\mu$. Target-specific microparticles which are specific for intravascular targets will preferably have a mean diameter of $>1\mu$, and more preferably $2-5\mu$. When they are specific for extravascular targets, they will preferably have a mean diameter of $<1\mu$.

Cores

The microparticle core material is "a gas and/or a liquid," which intends that it comprises a gas, a liquid, a mixture of gases, a mixture of liquids, or a mixture of gas(es) and liquid(s). Suitable core material must also be pharmacologically acceptable, i.e. biocompatible and having minimal toxicity. Examples of such suitable core material are well-known in the art. See, for example, U.S. Pat. No. 5,409,668 which discloses the use of microbubbles of gas as in vivo imaging agents, any of which could be used as core material in the present invention.

In general, suitable core materials can be divided into three categories: 1) water-soluble gases such as air, carbon dioxide, nitrogen, oxygen, nitrous oxide, helium or argon; 2) water-insoluble gases (having a solubility less than 0.01 mL/mL of water under standard conditions) such as sulfur hexafluoride or perfluoroalkanes such as perfluoropropane; and 3) chemicals that are liquids at temperatures below physiological temperature, such as perfluoropentane or other halogenated hydrocarbons. Particularly preferred are gas-liquid mixtures, for example a mixture of air or a low boiling point (gaseous) perfluorocarbon such as perfluoropropane, and a high boiling point (liquid) perfluorocarbon such as perfluoroheptane. These gas-liquid mixtures provide for a hydrophobic barrier within the microsphere shell, which serves to decrease the rate of gas exchange between the microsphere and the surrounding aqueous environment. See, for example, co-pending U.S. patent application Ser. No. 08/660,480.

Shells

The exterior surface of the microparticles are defined by a proteinaceous shell, and are thus referred to as "protein-shelled microparticles." Proteinaceous shell-forming material includes both naturally occurring filmogenic proteins, proteins made by methods involving recombinant DNA, and chemically synthesized proteins and amino acid polymers, which are collectively referred to herein as "proteins." Suitable proteins must be "filmogenic," which intends a soluble protein that is able to form a shell or film around the core material when the protein is insolubilized.

Examples of naturally occurring proteins include gamma-globulin (human), apo-transferrin (human), β-lactoglobulin, urease, lysozyme, and albumin. Human serum albumin is a preferred shell material. Chemically synthesized amino acid polymers which are useful in the present invention can optionally be in the form of block or random co-polymers combining both hydrophobic and hydrophilic amino acids in the same or different amino acid chains.

The stabilized microparticles are further characterized as having proteinaceous shells whose exterior surfaces have been tanned. "Tanning" refers to the use of metal salts such as chromium III potassium sulfate to form polynuclear coordination complexes between the ionized carboxyl groups of the surface-exposed amino acids, and bridging ligands such as hydroxol, oxo and sulfato groups. Other salts for tanning microparticles such as sulfates of zirconium, titanium and aluminum may also be used. Accordingly, suitable shell material must also exhibit free carboxyl groups on the surface of the microparticles and be capable of forming such coordination complexes.

Tanned microspheres exhibit the remarkable qualities of stronger, yet flexible shells. The increased strength of the shell allows it to survive longer once it is introduced into the body. The flexible quality of the shell allows for transit through the capillary system. Furthermore, the tanned shell imparts properties which allow for rigorous post-processing heat and chemical reactions. This enables the microsphere preparations to be further modified in such a way as to yield additional longevity and/or targeting abilities. It is additionally envisioned that these heat-stable microspheres may be sterilized at approximately 120° C. in an autoclave with no ensuing degradation. Without prior metal stabilization, microspheres are irreversibly damaged by temperatures above 75° C.

Manufacture of Protein-shelled Microparticles

Protein-shelled microparticles can be made by any known method, such as subjecting a mixture of an aqueous solution of a heat-insolubilizable protein and gas or liquid vapor to mechanical or ultrasonic cavitation as described in co-pending U.S. application Ser. No. 08/662,983 or PCT Number WO 95/01187. Alternatively, any suitable, commercially available proteinaceous microparticle preparation may be used, such as ALBUNEX® (Molecular Biosystems, Inc., San Diego, Calif.).

The Tanning Process

Conventional microparticle shells are stabilized and strengthened by tanning the shells with acidic metal salt solutions. Preferably, the metal salts are those typically used for leather tanning treatments. Most preferred is chromium. Tanning processes have enjoyed wide use in the leather industry. See, for example, Elvers, B., et al., *Ullmann's Encyclopedia of Industrial Chemistry*, $5^{th}$ ed., A15:268–274 (VCH Publishers, New York, 1990). Even so, the use of metal salts for stabilization of proteinaceous, in vivo preparations is a new utility for this process.

The process duration can be from as little as a few minutes to as long as several hours or more, depending on the temperature used. The process may be conducted at room temperature or with elevated temperatures (e.g., 85–160° C.) to speed the process. In order to avoid disruption of the shell material, the procedure is carried out in a closed system such that the pressure that builds in the headspace of the chamber counterbalances the increased pressure inside the microparticle shells.

The process is performed with constant agitation so that the protein shells do not clump together. Agitation is continued until the treated microspheres are cooled. Low speed centrifugation may be used to speed the separation of the microspheres for collection. The microparticles are collected and repeatedly washed with an aqueous solution (e.g., water or saline) which may optionally contain a buffer. The aqueous solution may further be saturated with the same gas and/or liquid as is present in the core material of the microspheres. The resulting metal content is determined by ICP or by other suitable methods.

The metal content of the tanned shell is variable, depending on the temperature, metal concentration and duration of the tanning process. Any person skilled in the art may determine the degree of tanning required for the particular application desired. For example, a higher degree of tanning would be required for target-specific microparticles than would be needed for those used in organ perfusion studies. The resulting bound metal content is approximately 0.1–100 μg/mL of microsphere suspension. These final contents may be obtained by using approximately 1–30 mM initial concentrations of metal salt solutions.

Recirculation

Tanned microspheres can be distinguished by their increased stability and longevity both in vitro and in vivo. Table 1 and Table 2 demonstrate in vitro and in vivo experiments further described in Examples 10 and 11, respectively, with various microsphere preparations, with and without the tanning of the shells. By reviewing the results of these experiments, any person skilled in the art can appreciate the substantial stabilizing effect of the metal treatment, both in vitro and in vivo. Furthermore, the results demonstrate the additive effect of the chromium treated shells when used in conjunction with a hydrophobic core.

TABLE 1

In Vitro Ultrasound Stability of Various Microsphere Preparations

| Preparation[1] | Gas | Hydrophobic[3] Compound | Chromium Treatment | MPS (um)[4] | Continuous Sonication Stability (min) | Intermittent Sonication Stability (hr) |
|---|---|---|---|---|---|---|
| 1 | Air | — | − | 3.4 | 12 | 1.1 |
| 2 | Air | — | + | 3.0 | 60 | 4.3 |
| 3 | Air | $C_5F_{12}$(10° C.) | − | 4.0 | 30 | 1.7 |
| 4 | Air | $C_5F_{12}$(10° C.) | + | 4.2 | 75 | 5.8 |
| 5 | Air | $C_6F_{14}$(21° C.) | − | 4.5 | 40 | 2.3 |
| 6 | Air | $C_6F_{14}$(21° C.) | + | 5.3 | 100 | 5.5 |
| 7 | Air | $C_7F_{16}$(14° C.) | − | 4.2 | 60 | 2.3 |
| 8 | Air | $C_7F_{16}$(14° C.) | + | 4.2 | 85 | 5.5 |
| 9 | Air | $C_8F_{18}$(18° C.) | − | 4.3 | 60 | 2.3 |
| 10 | Air | $C_8F_{18}$(18° C.) | + | 3.9 | 100 | 5.0 |
| 11 | PFP | — | − | 3.6 | 12 | 1.1 |
| 12 | PFP | — | + | 3.5 | 65 | 5.0 |
| 13[2] | PFP | — | − | 4.7 | 11 | 1.5 |
| 14[2] | PFP | — | + | 4.6 | 75 | 5.0 |

[1]Microspheres made by continuous sonication system (unless indicated otherwise).
[2]Microspheres made by mechanical cavitation.
[3]Numbers in parentheses are bath temperatures at which the hydrophobic compound was kept while bubbling gas through.
[4]Mean particle size as determined by the multisizer (Coulter ®)

TABLE 2

In Vivo Duration of Echogenicity

| | Air-filled | Air-filled Microspheres Chromium Treated |
|---|---|---|
| Dose (ml) | 1.0 | 1.0 |
| MPS (um) | 3.4 | 4.0 |
| Concentration (× 10$^8$/ml) | 5.5 | 3.9 |
| Visibility in LV (min) | 0.2 | 8.0 |
| Visibility in RV (min) | 0.3 | 7.8 |
| Myocardial perfusion[1] | No | Yes |

[1]With a dose ≧ 0.3 ml.

Uptake by the reticuloendothelial system ("RES") via phagocytosis by the Kupffer cells of the liver shortens the length of time particulate matter will remain in circulation. Target-specific microparticles in particular must be stable in circulation in order for them to have the opportunity to accumulate at their intended target. The efficiency of microparticles as ultrasound contrast agents can be improved by increasing their time in circulation by tanning the shell and adding functional groups to the particle surface that will prevent recognition by the RES.

It has been demonstrated that particulate matter, such as liposomes or colloidal particles, can be made "invisible" to the RES by steric shielding of negative charges on the particle surface (Lasic, D. D., et al., *Biochim. Biophys. Acta* 1070:187–192 (1991)). Such shielding keeps the particulate matter from interacting with opsonins, plasma proteins thought to be responsible for the removal of conventional liposomes by the RES. Shielding of microparticles can be accomplished by using hydrophilic functional moieties to form "hydrophilic microparticles." This allows them to remain in circulation for extended periods of time following intravenous administration. Suitable hydrophilic functional moieties include but are not limited to, polysaccharides, polyethylene glycols (PEGs), and peptides.

Because of the necessity for target-specific microparticles to remain in circulation long enough to reach their target and accumulate, their exterior surfaces are preferably neutral or hydrophilic. When the targeting moiety is itself hydrophilic, or the targeting moiety is attached via a hydrophilic spacer arm, it may not be necessary to further hydrophilize the exterior microparticle surface with a separate hydrophilic moiety or group. If the targeting moiety is not itself hydrophilic, the targeting moiety and a hydrophilic molecule may be attached independently to the exterior surface of the microparticle to render the microparticle both target-specific and hydrophilic.

Typical chemical reactions used to add hydrophilic groups to the surface of microparticles require that the particles be able to retain their gas/liquid cores during exposure to organic solvents, extremes of temperature, pH, and ionic strength, and the rigors of mechanical mixing in a reaction chamber. For these reasons, it can be appreciated that the enhanced stability of tanned microspheres makes them much better suited to serve as substrates for the addition of surface hydrophilic groups than their untanned counterparts. Untanned microparticles would be able to survive only a very limited subset of desirable reaction conditions.

Attachment of Functional Moieties

A functional moiety can be attached to a stabilized protein-shelled microparticle using any of a wide variety of known chemical reactions. Various combinations of reactive chemical groups are known. For example, a succinimidyl ester group will form an amide bond when reacted with an amino group. Other examples are given in Table 3.

TABLE 3

Combinations of Reactive Groups

| Nucleophile | Reactive Group |
|---|---|
| amine, hydrazide, hydrazine | active ester, anhydride, acid halide, sulfonyl halide, imidate ester, isocyanate, isothiocyanate, chlorofomate, carbodiimide adduct, aldehyde, ketone |
| sulfhydryl | haloacetyl, alkyl halide, alkyl sulfonate, maleimide, α, β-unsaturated carbonyl, alkyl mercurial, sulfhydryl, α, β-unsaturated sulfone |

The preference of any given method is dictated by the nature of the targeting moiety (solubility, presence of other reactive groups, etc.) and the specific site of attachment. It is also important that the method chosen does not appreciably interfere with or destroy the functional moiety, which in the case of a targeting moiety would mean destruction of its ability to complex with the target tissue/organ.

It is also possible to attach a targeting moiety to the exterior surface of a stabilized microparticle by means of a linking agent, or spacer arm. (See, for example, U.S. Pat. No. 5,225,182.) The spacer arm may additionally be bifunctional. The term "bifunctional" as used herein intends a molecule with two different ends, each possessing a different functional group for use in coupling reactions, one of which is used to attach to a functional group on the exterior surface of a microparticle, and the other of which is used to attach to a functional group of a targeting moiety. The functional group of a targeting moiety may be protected by a protecting group for subsequent deprotection and attachment of the targeting moiety.

The spacer arm must be biocompatible and provide a sterically free binding site for the targeting molecule. The spacer arm may also act as a hydrophilizing agent, or the hydrophilicity of the microparticle exterior surface may be provided by another molecule as described above. Preferably, the spacer arm will be greater than 20 Å in length. In addition, the spacer arm must be resistant to cleavage by the chemical manipulations involved in preparation of the imaging agents, and also must be resistant to the shearing forces present during injection and circulation of the microparticles. Suitable bifunctional spacer arms include, but are not limited to, polyethylene glycol, dextrans, modified starches, chitosans, heparin, chondroitin sulfates, polyvinyl alcohol, and polyacrylic acids, or the derivatives of any of these molecules. PEGs are most preferred as spacer arms.

Other Methods Relating to Tanned Microspheres

There are still numerous reactive groups on the outer surface of a tanned proteinaceous microparticle. They consist mostly of carboxyl and amino groups. If necessary, the stabilized microparticles can be pretreated with a polyamine such as spermine, polylysine or polyallylamine in presence of a water-soluble carbodiimide, in a pH range of 6–8, for 6 to 24 hours in order to increase the amine concentration of the shell surface by covalent attachment of polyamine. Under similar conditions, a polycarboxyl acid such as citric acid, polyglutamic acid or polyacrylic acid can also be reacted with free $\epsilon$-amino on the microparticle with the purpose of increasing the carboxyl density on the shell surface. In either case, simple washing and centrifugation delivers microparticles with different surface properties.

Figure 2:
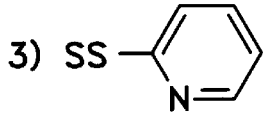
FIG. 2 depicts the general formulas of activated PEGs.
Figure 2:
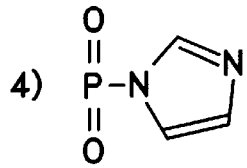
Figure 2:
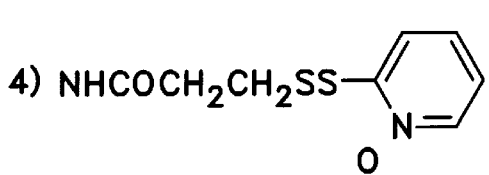
Figure 2:
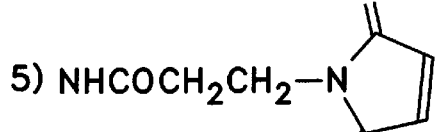
Figure 2:
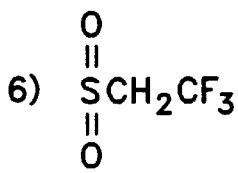
Figure 2:
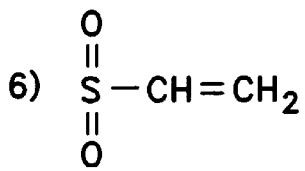
Figure 2:
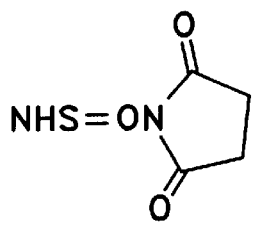

In order to bind ligands to a microparticle surface, one can either activate the carboxyl groups (for example with a water-soluble carbodiimide) and react them with a nucleophile such as an amine derivative of Polyethylene glycol (PEG) to give a stable amide linkage, or use an active PEG derivative which can react with the free $\epsilon$-amino groups of the lysines (referred to collectively as "PEGylation"). There is a large array of possible reactive PEG derivatives to choose from (see FIG. 2). Preferred are PEG derivatives in which one of the terminals is an active ester group, such as a succinimidyl ester, or a succinimidyl carbamate ester, which both undergo aminolysis and give stable amide or urethane linkages, respectively. Another favored choice is to use PEG derivatives which have alkylating properties such as tresyl esters or epoxides. These agents have the advantage of preserving the net surface charge of the microparticle during the PEGylation process by transforming the primary amines on the microparticle surface into secondary amines. FIG. 2 shows the structure of PEG derivatives with different active terminals. Any combination of Y and Z is useful for making PEGylated microparticles with or without target specificity. Monofunctional PEGs (Z=1 or 2) are used to surround the microparticles with a neutral hydrophilic layer. Such a particle will be less detectable by the RES and have increased circulation time.

This approach of attaching target specific ligands is tailored specifically to proteins substantially lacking free thiol groups, for example, serum albumin derived microparticles. The serum albumin derived microparticle has virtually no free thiol groups on its surface since 34 of the 35 cysteine groups present in albumin are linked to each other via disulfide bridges. However, there are many free amine functions. One of our preferred approaches is therefore to choose a heterofunctional PEG in which Y represents an active ester or alkylating moiety which are amine selective, and in which Z represents a thiol-selective group (FIG. 2: Z=3,4,5 or 6). Some of these heterofunctional PEGs are commercially available (Shearwater Polymers, Inc., Huntsville, Ala.). Others can be easily synthesized using known methods by anyone skilled in the art.

Other Attachment Methods

Although the aforementioned methods for attaching functional moieties to the tanned microparticles are suitable for many applications, there are circumstances during which it is desired to use a specialized conjugation technique. For instance, it is sometimes desired to attach a functional moiety using techniques that allow for maximization of coupling efficiency to minimize cost or techniques which would enable convenient conjugation of two or more different functional moieties.

Figure 3:
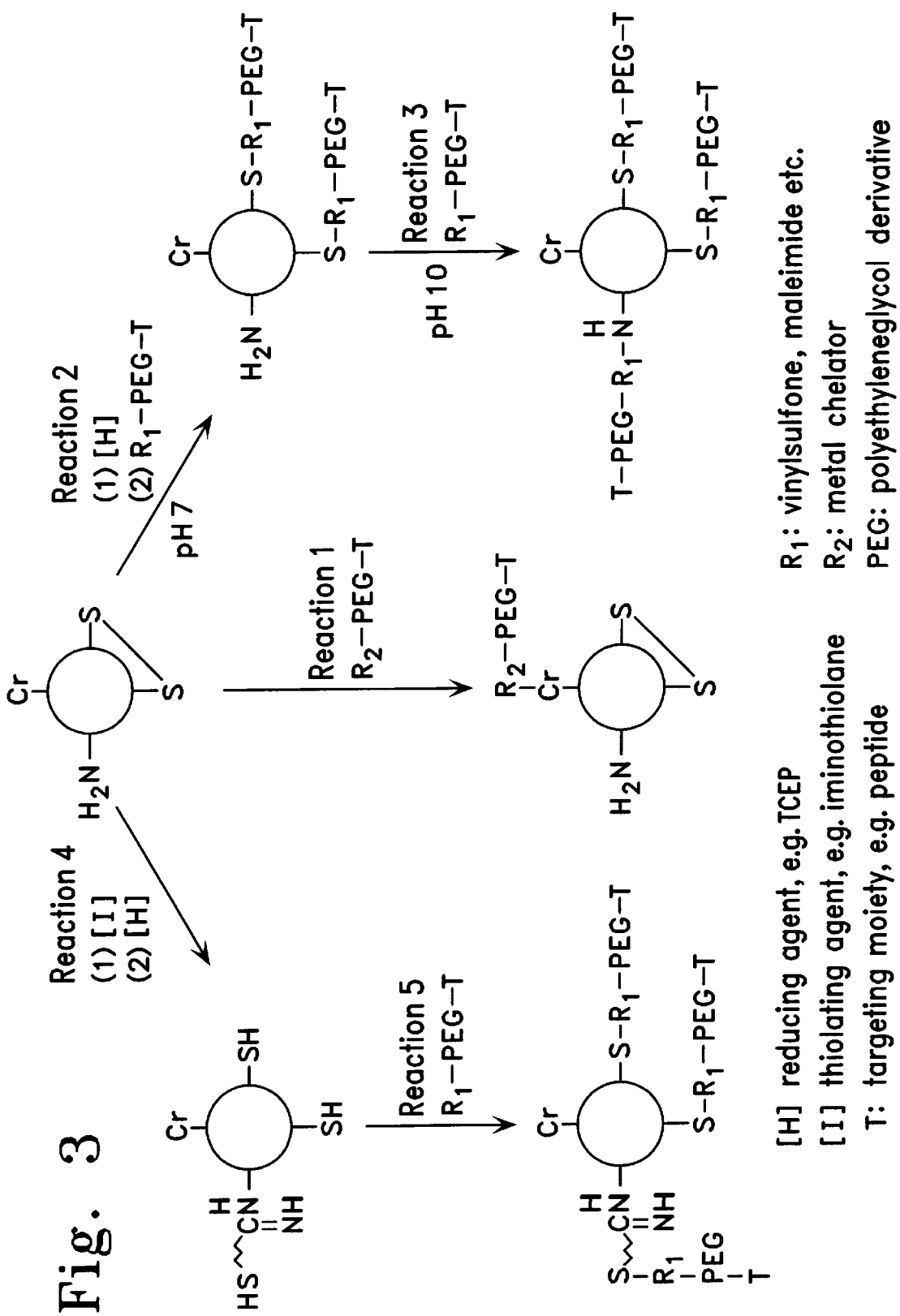
FIG. 3 depicts a flow diagram of various attachment protocols for attaching functional moieties to the surface of tanned microparticles.

As described above, it is possible to attach functional moieties to the available amino groups on the outer surface of the tanned microparticles. One disadvantage of attaching functional moieties which contain active esters to these amino groups is that active esters are susceptible to hydrolysis during the conjugation procedure, which limits conjugation efficiency. In addition, active esters of relatively large functional moieties, such as polyethylene glycol-peptide complexes, may not be able to react with the surface exposed amino groups because of steric hinderance. Accordingly, coupling efficiency may be improved by utilizing other methods of attachment to the surface of the tanned microparticles. As shown in FIG. 3, after chromium treatment, the resultant tanned microspheres (shown at the top of FIG. 3) contain surface exposed chromium, disulfide groups and amino groups, which are available for a variety of chemical reactions as described below.

Mordant Dyes

As a result of the tanning process, chromium is also present on the outer surface of the microparticles. Through a "metal fixation" mechanism, this surface-exposed chromium can be used as a de novo site of attachment of functional moieties such as target-specific ligands. We have discovered that it is possible to employ complexation mechanisms that are normally associated with the textile industry to make such attachments to the tanned microspheres of the present invention. Chrome dyes have been used for a long time in the wool dyeing industry. They provide good general color fastness properties to the fiber. The so-called "mordant dyes" are a subgroup of the chrome dyes and are applied to the fiber after it has been chromium-treated. Complex formation occurs during the dyeing process, usually in an acidic medium under participation of electron donors. Chromium, the central atom of the complex acts as a link between the dye and the fiber. This results in a strong bond which is reflected in the excellent color fastness obtained when applied to textiles.

The dyes must contain suitable functional groups. The binding of $Cr^{3+}$ occurs then by substitution of the H in COOH, or OH groups, and via lone electron pairs from —(C=O)—, —$NH_2$, etc. This principle can be applied to chromium treated protein microparticles to attach functional moieties which are complexed to the chromium via terminal groups that have "mordant" qualities, i.e. the ability to chelate the chromium. Such terminal groups can be, for instance, salicylic acid or alizarin-type compounds. Virtually any compound with such qualities can be used, and are well known to one of skill in the art. It is important, however, that the stability of the chromium-chelator complex is not greater than the stability of the protein-chromium complex, otherwise the chromium could be detached from the microparticle surface during the reaction. Using this method of attachment, it is possible to form stable linkages with any of the functional moieties described herein, inter alia, targeting moieties, polymers (synthetic hydrophilic polymers, polysaccharides, proteins, etc.) Such stable linkages is desirable for preparing microparticles for commercial use where long shelf life is a desirable characteristic.

A representative embodiment of the aforementioned method of attachment is shown in Reaction 1 of FIG. 3. As shown, it is possible to render tanned microspheres hydrophilic, and thus less detectable in vivo by the RES, by attaching PEG. At the same time, using a peg-targeting moiety ("PEG-T") complex, the microparticles can be rendered target specific. Amino derivatized polyethylene glycol with a targeting moiety attached thereto (amino-PEG-T) can be reacted with 5-chlorosulfo-salicylic acid to form a stable sulfonamide linkage $R_2$-PEG). The resultant PEG derivative will then contain a salicylic acid group ($R_2$) which, as depicted in Reaction 1 of FIG. 3, is capable of forming a stable metal complex with chromium on the surface of the tanned microparticles. For instance, the attachment can be accomplished at elevated temperature, typically at 95° C., with stirring in an autoclave.

Thiol Linkages

It is also possible to utilize the existing disulfide groups on the surface of the tanned microparticles as a site of attachment of functional groups. As shown in Reaction 2 of FIG. 3, the disulfide bonds are reduced using typical reducing agents, such as 2-mercaptoethanol or dithiothreitol. A preferred reducing agent is tris-(2-carboxyethyl) phosgene (TCEP). Chromium treated microparticles are stable during the reduction process. Excess reducing agent is removed, and the resultant microparticles are washed in the absence of oxygen. The resultant thiol groups are capable of participating in hydro-alkylthio-additions with alkene or alkyne groups. For example, vinylsulfone or maleimido groups ($R_1$) are known to be very selective for reactions with sulfhydryls at very mild conditions at pH 7. Vinylsulfone is preferable over maleimide because of its greater hydrolytic stability in water. Such stability has a distinct advantage over active ester modified PEG, which is susceptible to hydrolysis under attachment conditions. Accordingly, the vinylsulfone derivatized PEG-peptide conjugate ($R_1$-PEG-T) can be efficiently attached to the microparticle surface via a very stable thioether linkage (Reaction 2 of FIG. 3.) After the attachment procedure is over, the unreacted thiol groups are oxidized to form disulfide bonds under mild oxidative conditions. Vinylsulfone groups have the additional advantage to undergo hydro-amino additions. Thus, a vinylsulfone group will react slowly with amine groups at pH 9–11 (Reaction 3 of FIG. 3.) This allows the $R_1$-PEG-T to not only attach to the thiol groups, but also to some extent to amino groups. This can enable conjugation of two different vinylsulfone-activated functional moieties, one which reacts at neutral pH and attaches to the thiol groups and another which reacts at higher pH and attaches to the amino groups.

It is also possible to introduce additional thiol groups to the surface of the microparticles by pre-thiolation of the amino groups. As shown in Reaction 4 of FIG. 3, thiol groups can be introduced by exposing the microparticles to thiolating agents, such as iminothiolane ("Traut's reagent"; "T"). The existing disulfide bonds on the surface of the microparticles can then be reduced with TCEP ("H") as shown under acidic conditions. Then, as shown in Reaction 5 of FIG. 3, $R_1$-PEG-T can be attached to both amino groups that have been converted to thiols and to the existing thiol groups formed by reduction.

Vinylsulfone-PEG derivatives can easily be made by someone skilled in the art, for instance, by attaching vinylsulfonylpropionic acid to a PEG derivative with a suitable terminal. Vinylsulfonyl and maleimido PEGs are also commercially available from Shearwater Polymers, Huntsville, Ala.

Target Specificity

The stabilized microparticles of the present invention may be further functionalized to render them "target-specific." The stabilized microparticles of the present invention are particularly well-suited for the production of target-specific microparticles, since their increased strength allows for heat stability and rigorous chemical post-processing and also assures that the microparticles possess the in vivo longevity needed to reach their target and accumulate. In order for intravenously administered target-specific microparticles to achieve this goal, they must withstand the physical forces encountered in the circulatory system and they must exhibit chemical and biological stability under physiological conditions. A target-specific microparticle is considered "stable" if it persists in vivo for a sufficient length of time for the desired enhancement of the ultrasonic image of the target tissue/organ to be achieved.

"Target-specific" microparticles are further characterized as having a preferential affinity for the target cell type, tissue or organ, and are capable of forming complexes with the target, which will necessarily result in a greater tendency for them to accumulate in or near the target tissue/organ than to stay in circulation. The rate and degree of accumulation in or near the target must also be sufficient to provide enough ultrasonic reflectivity, i.e. "signal," to distinguish from background reflectivity, i.e. "noise."

A "target tissue" or "target organ" is any structure or location in the body that can be identified and differentiated from non-target tissues/organs by the presence of particular target-specific substituents, such as proteins, carbohydrates, glycoproteins, or glycolipids localized on cell surfaces or on extracellular matrix material. In order to be suitable as a target, these target-specific substituents must be capable of being selectively recognized by a particular targeting moiety.

The target tissue/organ may be contained within the endothelial walls of the vascular system ("intravascular target"), or it may lie outside of the confines of the vascular endothelia ("extravascular target"). Suitable intravascular targets include, but are not limited to: cardiovascular lesions such as atherosclerotic plaques, thrombi and emboli. See U.S. Pat. No. 5,364,612 for examples of suitable intravascular targets. Suitable extravascular targets include, but are not limited to: liver, kidney gastrointestinal tract, reproductive organs, urinary system, breast, lung, and cancers thereof such as lymphomas, melanomas, gliomas, sarcomas and neuroblastomas.

In order for the target-specific microparticles of the present invention to be useful for imaging of a particular target tissue or organ, the target must be accessible by the microparticles via the circulatory system. This requires that the shell maintains flexible properties which enable movement through the capillary system. Since microparticles within the size range that are most easily imaged using current medical ultrasound technology (generally 1–10$\mu$) have a tendency to remain in the intravascular spaces, intravascular targets are preferred. Extravascular targets which are accessible by smaller (<1$\mu$) microparticles, e.g., via sinusoidal junctions in the capillary endothelia of the liver and spleen, must also be sufficiently vascularized for the intravenously administered microparticles to reach their intended target. Thus, certain of the more dense tissues which are poorly vascularized, such as some solid tumors, may thus be relatively inaccessible by the microparticles. Although, it is well known that vascular permeability can be increased by vasodilators, tumor necrosis factor, and other vasoactive agents. If this increased permeability is translated into enhanced extravasation of microparticles, the targeted microparticles would have better access to tumor target cells and would bind to them. Furthermore, other types of solid tumors have poorly organized and fragile vascular systems which actually increase their accessibility by microparticles.

Targeting Moiety

Complex formation between a target-specific microparticle and the target tissue/organ is achieved by attaching a targeting moiety to the external surface of the tanned microparticle shell. A targeting moiety is chosen which is capable of forming a stable complex with the target-specific substituent of the target tissue/organ. The choice of targeting moiety will necessarily depend on the nature of the target-specific substituent with which it will form a complex. For example, somatostatin can be used to target pancreatic β-cells, endorphins can be used to target regions of the brain, or insulin can be used to target fat cells.

The targeting moiety may be any tissue/organ-specific ligand, such as a ligand which binds to a specific cell surface receptor, or an antibody with an affinity for a particular cell type. Suitable ligands include, but are not limited to, oligosaccharides, polysaccharides, peptides, proteins, glycopeptides, glycoproteins, or glycolipids. For example, to target microparticles to the liver, hepatocyte-specific ligands may be employed. Mammalian hepatocytes possess asialoglycoprotein receptors on their plasma membranes which interact with glycoproteins whose oligosaccharide chains have β-linked galactose or N-acetylgalactosamine terminals (Ashwell, G. et al., *Adv. Enzymology* 41:99 (1974). It has been shown that when particles such as liposomes have galactose bound to their surface, they become hepatocyte-specific. It has also been reported that arabinogalactan, a water-soluble carbohydrate obtained from Western larch wood (*Larix occidentalis*), interacts with asialoglycoprotein receptors of hepatocytes (Beuth, J., et al., *Cancer Res. Cin. Oncol*. 113:51–55 (1987). This principle has been applied for making hepatocyte-specific MR agents from iron oxide particles coated with arabinogalactan (Josephson, L., et al., *Magn. Res. Imag*. 8:637–646 (1990). Coating stabilized gas and/or liquid-filled microspheres with an arabinogalactan layer (mean particle size 0.1–1 μm) would make them hydrophilic and invisible to the Kuppfer cells of the liver and at the same time they would also be hepatocyte-specific. By filling the particles mostly with liquid perfluoropentane, the microspheres would be small enough to pass through the sigmoidal junctures of the liver. By application of ultrasound energy, the liquid chemical becomes volatilized at body temperature (~37° C.) and produces gas microbubbles in a size range which produces backscatter with diagnostic ultrasound (0.5–5 μm). Various other targeting moiety/target-specific substituent combinations would be apparent to one of skill in the art.

Antibodies which are specific for particular tissues/organs may also serve as suitable targeting moieties. Such antibodies may be polyclonal, but are preferably monospecific, and more preferably monoclonal. An "antibody" is an immunoglobulin molecule capable of specific binding to a target through at least one antigen recognition site, located in the variable region of the immunoglobulin molecule. As used herein, the term encompasses not only intact antibodies, but also fragments thereof, mutants thereof, fusion proteins, humanized antibodies, and any other modified configuration of the immunoglobulin molecule that comprises an antigen recognition site of the required specificity.

An antibody is referred to as "specific" if it binds via at least one antigen recognition site to the intended target more frequently, more rapidly, or with greater duration than it does to alternative substances. An antibody is capable of "specifically delivering" a microparticle if it conveys or retains that microparticle near a particular target substituent or antigen more frequently than to other non-targeted cell types or antigens.

Suitable antibodies would be those directed against antigens which are specific to any particular target tissue or organ. See, for example: Wang, et al. for platelet-specific antibodies (Nucl. Med. Biol 18(3):275–280 (1981)); Bini, et al., for fibrinogen- and fibrin-specific antibodies (Arteriosclerosis 9(1):109–121 (1989)); Knight, et al., for fibrin-specific antibodies (Nuc. Med. Comm. 9:823–829 (1988)); Milenic, et al., for carcinoma-specific antibodies (Cancer Res. 51:6363–6371 (1991)); Goldenberg, et al., for tumor-specific antibodies (J. Nuclear Med. 33(5):803–814 (1992).)

The targeting moiety can also be comprised of a multi-specific antibody conjugate comprising an immunoreactive multispecific composite of at least two different substantially monospecific antibodies, or fragments thereof. Preferably, the composite comprises antibodies or antibody fragments that specifically bind to one type of leukocyte and antibodies that specifically bind to antigens associated with intracellular targets, such as leukocytes, fibrin, myosin or platelets. Such a targeting tool is described in U.S. Pat. No. 5,364,612, and is particularly useful for targeting cardiovascular lesions such as atherosclerotic plaques; vascular clots such as thrombi or emboli; and organ infarcts, such as myocardial infarctions. It is further envisioned that the microsphere-antibody complex can be used as both an acoustic diagnostic agent as well as a therapeutic delivery agent.

In addition to the aforementioned targeting moieties, it is also possible to attach RGD peptides as described in Bioorganic and Medician Chemistry, 3(4): 337–360 (1995).

Use of Stabilized or Functionalized Microparticles as Ultrasound Contrast Agents The microparticles of the present invention are used in the form of a suspension in a sterile, aqueous, injectable carrier. Such carriers are well known in the pharmaceutical formulation art. The concentration of microparticles in the suspension will normally be in the range of $1 \times 10^7$ to $1 \times 10^{10}$, more usually $1 \times 10^8$ to $1 \times 10^9$, per mL of suspending medium. Saline solution is a preferred carrier. Naturally, the microparticles may be kept in more concentrated or more dilute suspensions than specified above and then reformulated for injection.

In such use, the suspension is injected into a peripheral vein at about 0.05 to 0.5 cc per kg body weight, or alternatively, continuously infused at a low concentration. Any other suitable route of administration is acceptable and could include intravaginal and rectal administrations. After allowing the imaging agent to accumulate at the target site, ultrasonic energy is applied to the tissue/organ to be imaged and reflected energy is collected and translated into an image using any ultrasound imaging equipment. These modalities include fundamental (B-mode), Doppler, 3-dimensional, and harmonic imaging.

Other Uses of Stabilized or Functionalized Microparticles

Although the present specification has focused primarily on the use of the aforementioned microparticles in the preferred embodiment of ultrasonic imaging, it is also understood that such microparticles would be useful in MRI and CT imaging, as well as in therapeutic applications. These other uses would require incorporation of an appropriate microparticle core. For example, microparticles which incorporate sufficient magnetically equivalent fluorines in their core can be used in MRI; microparticles which incorporate sufficient radionuclides such as $I^{125}$ in their core can be used in CT; and microparticles which incorporate sufficient therapeutic agents can be used in therapeutic applications. The term "sufficient" as used herein refers to that amount which is necessary to achieve the desired diagnostic or therapeutic affect.

EXAMPLES

Example 1

Preparation of Liquid-Filled Microparticles

A 2" Gaulin colloid mill apparatus was plumbed with a stainless steel gas inlet line and a stainless steel liquid inlet line. Both lines were fitted with heat exchangers to warm the incoming protein solution and convert liquid perfluoropentane to a vapor. The outlet port from the mill was connected to a stainless steel chiller. Perfluoropentane was delivered into the gas inlet line with a syringe pump (Harvard Apparatus Co.) fitted upstream of the heater so that liquid perfluoropentane could be vaporized and introduced into the mill as a gas.

One percent human albumin solution (U.S.P.) was heated to 60° C. and pumped into the mill at 300 ml/min. Air, used as a carrier gas was pumped through the gas line at 0, 40, or 80 ml/min. and liquid perfluoro-n-pentane was introduced via the syringe pump into the gas line at 3.5 ml/min. The perfluoro-n-pentane or air/perfluoro-n-pentane mixture was heated to 90° C. with the in-line heat exchanger. The mill was run at 20,000 rpm, 0.015 in. gap, at an approximate temperature of 76.5° C. The chiller cooled the milled product to 10–20° C.

The suspensions of microparticles emerging from the chiller were collected in glass bottles. Upon standing for several hours at 4° C., the suspension separated into a layer of microparticles on the bottom of the bottles, an intermediate clear liquid layer, and a foam upper layer. The microparticles and clear liquid were drained from the bottles and stored in closed glass vials at 4° C.

Example 2

Preparation of Gas-filled Microparticls

A) Continuous Sonication System

The method described in U.S. Pat. No. 4,957,656 was used to prepare perfluoropropane and sulfur hexafluoride microparticles as follows:

Human serum albumin was diluted to a 1% w/v solution with sterile saline. The solution was heated to incipient denaturation, approximately 76° C. The system was closed to the external atmosphere and perfluoropropane or sulfur hexafluoride gas was introduced into the liquid in place of air. The product was made continuously by flowing the gas/albumin mixture (1:1 v/v) past the sonicator horn at approximately 100 ml liquid/min. The product was chilled upon exit from the sonication chamber by passage through a heat exchanger and collected as a bulk liquid suspension of microspheres. Handling and storage conditions were similar to that given for manually produced microspheres.

B) Mechanical Cavitation

Albumin microspheres containing perfluoropropane or sulfur hexafluoride gas were also produced in a closed system by milling a mixture of 1% human serum albumin and gas. Albumin solution, heated to a temperature sufficient to allow microsphere formation by the mechanical cavitation of a given mill, was mixed 1:1 (v:v) with gas and introduced into a colloid mill. The liquid flow rate was dependent upon the capacity or size of the mill, and was typically 100 to 500 ml/min. The outflow from the mill was cooled by passage through a heat exchange system and the resulting albumin microsphere suspension was collected in bulk. The product was filled into glass vials, similar to the other processes.

Example 3

Preparation of Gas-filled Particles with a Hydrophobic Barrier

A carrier gas (air, perfluoropropane) was saturated with a hydrophobic compound such as perfluorohexane by bubbling it via a fritted gas dispersion tube through the hydrophobic compound which was maintained in a constant temperature bath as described in co-pending U.S. patent application Ser. No. 08/660,480. The temperature was adjusted to the appropriate level to maintain the required partial vapor pressure. The temperature of the gas line leading to the cavitation chamber was maintained at or above the bath temperature in order to prevent condensation of the hydrophobic compound from the gas-vapor mixture before it reached the chamber. The gas/hydrophobic compound ratio was determined by taking a gas sample downstream of the gas bubbler and analyzing it by gas chromatography. The gas-vapor mixture was used to make microparticles in a continuous sonication system as described in Example 2.

Example 4

Chromium Treatment of Microparticles

A vial containing a suspension of perfluoropropane-filled microspheres in a saline solution of human serum albumin, was allowed to stand at room temperature until all microspheres had floated to the top, forming a dense layer. During the following manipulations, the microspheres were kept in a perfluoropropane (PFP) environment. The clear bottom layer was removed via syringe and replaced by a solution of a 5.6 mM chromium (III) potassium sulfate solution (deaerated and saturated with PFP). The mixture was heated in an oilbath at 95° C. for 10 minutes with stirring. The suspension was allowed to cool to room temperature while stirring. After standing overnight, the chromium containing lower layer was removed via syringe. The remaining microspheres were thoroughly washed by resuspending them in PFP-saturated saline. Upon removal of the washings, the microspheres were stored in PFP-saturated saline under a PFP atmosphere at room temperature. Coulter counter measurements indicated an initial particle concentration of $1.39 \times 10^9$/mL (mean size of 4.86 µm), while the final concentration of chromium treated microspheres was $1.15 \times 10^9$/mL (mean size of 4.65 µm). The bound chromium content of the microsphere suspension was 45 µg/mL as determined by ICP.

Example 5

Reaction of Microparticles with a Monofunctional PEG

A) Amination of Stabilized Microspheres

A suspension of chromium treated air/perfluoroheptane-filled microspheres, (approximately $5 \times 10^9$ in a solution of polylysine (25 mg, 3600 daltons, HBr salt) and 1-(3-dimethylaminopropyl)-3-ethylcarbodiimide-HCl (20 mg) in 0.2 M 3-(N-morpholino)-propane sulfonic acid (MOPS) buffer (pH 7.6, 2 mL, air- and perfluoroheptane-saturated). The particles were kept in suspension by gentle mixing for 5 hours, at room temperature. The aminated microspheres were repeatedly washed with saline with intermittent centrifugations and removal of contaminants.

B) PEGvlation of Microspheres

The aminated microspheres described in Example 5A above were suspended in 0.2M N-(2-hydroxyethyl) piperazine N'-3-propanesulfonic acid (EPPS) buffer, pH 8.0 (2 mL, saturated with air and perfluoroheptane) containing methoxy-PEG-epoxide, (60 mg, mol. weight 5000, Shearwater Polymers, Inc., see FIG. 2: Y=5, Z=1). The particles were kept in suspension by gentle mixing at room temperature for 50 hours. Finally they were washed with saline and stored in suspension.

Example 6

Reaction of Microparticles with a Heterofunctional PEG

Stabilized gas-filled microspheres (approximately $2 \times 10^9$ particles), for instance as described in Example 5A above, are suspended in 0.2 M perfluoroheptane/air-saturated EPPS buffer (1 ml; pH 8) and allowed to react with 30 mg of the heterofunctional PEG (with Y=2 and m=2, or Z=5 and n=120, as described in FIG. 2) for 4 hours, while gently mixing. The PEG derivative attaches to the particle surface via its lysine-active succinimidyl propionate terminal. The particles can be further PEGylated with a monofunctional PEG, for instance with Y=2 and Z=1 and n=25–50 (as described in FIG. 2) in order to further increase the hydrophilic surface layer. The resulting microsphere with its sulfhydryl-selective terminal will serve as universal acceptor for any thiol-containing ligand. If necessary, a targeting molecule will have to be thiolated before it can be attached. Besides antibodies and their fragments, other target-specific molecules such as peptides and oligosaccharides can also be used. Different combinations of PEG terminals are described in FIG. 2 and can be easily synthesized by using known methods by those skilled in the art.

Example 7

Attachment of a Targeting Ligand to Microparticles

PEGylated microspheres described above in Example 6 are incubated in a perfluoroheptane/nitrogen-saturated buffer (pH 7) with target-specific Fab' molecules. The Fab's react via free sulfhydryls with the thiol-selective PEG terminals on the microspheres.

Thiolated antibodies and F(ab')$_2$ fragments are attached in a similar way. Thiolation can be done, for instance, with N-succinimidyl-S-acetylthioacetate, S-acetylsuccinic anhydride or with 2-iminothiolane.

Example 8

Star PEGylation

Stabilized microparticles are also coated with star PEG molecules in the form of a hydrogel. Star PEGs are multi-armed molecules made by polymerization of ethylene oxide from a cross-linked divinylbenzene core. A star PEG molecule is typically activated with tresylchloride. Tresylated star PEGs are commercially available (Shearwater Polymers, Inc., Huntsville, Ala.). The microspheres are treated with tresylated star PEGs in an aqueous buffer (pH 10). The star molecules bind covalently, forming a dense layer on the microsphere. The linkage results from the reaction between amino groups on the microsphere and the tresylate terminals on the star molecule arms. Moreover, by limiting the reaction time (1 hour or less), microspheres are covalently coated with a monolayer of star PEG molecules which are still active due to unreacted tresyl groups. The coated microspheres are repeatedly washed and then allowed to react with a targeting ligand, such as an antibody or its Fab' fragment (pH 8.5–10.0). The ligands are covalently bound via their amino and thiol groups to the star PEGylated microsphere. The result is a target-specific microsphere preparation with extended in vivo lifetime.

Example 9

Covalent Linkage of Arabinogalactan to Microspheres

Purified arabinogalactan (23,000 daltons; Sigma Chemical Co.) is carboxymethylated with bromoacetic acid in the presence of a base, as can be done by anyone skilled in the art. The resulting carboxymethyl arabinogalactan is conjugated to the surface of, for example, chromium treated perfluoroheptane/air filled microspheres via lysine groups of the protein, by the action of a water-soluble carbodiimide, such as 1-(3-dimethylaminopropyl)-3-ethylcarbodiimide in a suitable buffer (pH 7.5). Finally, the microspheres are extensively washed with saline saturated with perfluoroheptane and stored as a suspension.

Example 10

In Vitro Ultrasonic Stability Determination

In a one liter plastic beaker, 800 mL of a constantly stirring saline solution were saturated with air at 37° C. Subsequently, an aliquot of a microsphere suspension was added so that the final concentration was approximately $1 \times 10^4$ microspheres per mL. The echogenicity was tested with an HP Sonos 100 ultrasound machine and a 5 MHz transducer. The testing was performed at a power setting of 30% and an 8 cm depth of field, with continuous or intermittent sonication. The intermittent sonication measurements were performed at regular time intervals (for approximately 10 seconds each) with the microsphere suspension being continuously stirred. The images were recorded on videotape and subsequently evaluated using the Image-Pro (Media Cybernetics) software program. The gray-scale intensities in a 200×80 pixel rectangle were plotted as a function of time. The results are shown in FIG. 1. (Air microspheres=–□–; air+chromium microspheres= –□–; air plus perfluorooctane microspheres=–⊗–; and air plus perfluorooctane plus chromium microspheres=–□–.)

The "continuous stability" measurements reflect how the microspheres hold up in an ultrasonic field, whereas the "intermittent stability" measurements give an indication of their physical stability during circulation in an air-saturated environment. The microspheres were considered "stable" if the grey scale remained greater than 15% above background.

Example 11

In Vivo Study

Chromium-treated air-filled microspheres were evaluated for enhancement of the right and left ventricle and also for myocardial perfusion. The test agent was kept at room temperature (22° C.) and resuspended prior to injection (via 18 G needle) into the femoral vein of an anesthetized New Zealand White rabbit (weight 3.5 kg). A suspension of air-filled microspheres (ALBUNEX®, Molecular Biosystems, Inc., San Diego, Calif.) was utilized as a control. The ultrasound imaging was performed with a 5 MHz transducer attached to an HP Sonos 1500 instrument and recorded on videotape. The agent provided both opacification as well as perfusion enhancement. The duration of enhancement of the LV, RV and myocardium were assessed by acoustic densitometry.

Modifications of the above-described modes for carrying out the invention that are obvious to persons of skill in the field of ultrasound contrast agents are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A composition comprising a suspension of stabilized microparticles, wherein said microparticles compose:
   (1) a core material comprising a gas and/or a liquid; and
   (2) a shell comprising a protein encapsulating said core material, wherein the protein is crosslinked via chromium-containing polynuclear coordination complexes;
   and wherein said microparticles are suspended in an aqueous carrier.

2. The composition of claim 1 wherein the protein is albumin.

3. The composition of claim 1 wherein the core material is a gas.

4. The composition of claim 3 wherein the gas is air.

5. The composition of claim 3 wherein the gas is a perfluoroalkane.

6. The composition of claim 1 wherein the core material is a liquid.

7. The composition of claim 6 wherein the liquid is a halogenated hydrocarbon.

8. The composition of claim 7 wherein the halogenated hydrocarbon is perfluoropentane.

9. The composition of claim 1 wherein the core material is a mixture of a first gas and a second gas.

10. The composition of claim 9 wherein the first gas is perfluoropropane and the second gas is perfluoropentane.

11. The composition of claim 1 wherein the core material is a mixture of a gas and a liquid.

12. The composition of claim 11 wherein the gas is air and the liquid is perfluoroheptane.

13. The composition of claim 11 wherein the gas is air and the liquid is selected from the group consisting of C5–C10 perfluorinated compounds.

* * * * *